(12) United States Patent
Brown et al.

(10) Patent No.: US 10,209,187 B1
(45) Date of Patent: Feb. 19, 2019

(54) METHOD FOR ATOMIC AND MOLECULAR SENSING

(71) Applicant: Triad Technology, Inc., Longmont, CO (US)

(72) Inventors: Archie T Brown, Longmont, CO (US); Frederick T Brown, Longmont, CO (US)

(73) Assignee: Triad Technology, Inc., Longmont, CO (US)

( * ) Notice: Subject to any disclaimer, the term of this patent is extended or adjusted under 35 U.S.C. 154(b) by 0 days.

(21) Appl. No.: 16/109,361

(22) Filed: Aug. 22, 2018

(51) Int. Cl.
*G01N 21/61* (2006.01)
*G02B 6/02* (2006.01)
*G02B 6/255* (2006.01)

(52) U.S. Cl.
CPC ......... *G01N 21/61* (2013.01); *G02B 6/02328* (2013.01); *G02B 6/2551* (2013.01); *G01N 2201/088* (2013.01)

(58) Field of Classification Search
CPC ............. G01N 21/61; G01N 2201/088; G02B 6/02328; G02B 6/2551
USPC ................................................ 356/429–448
See application file for complete search history.

(56) References Cited

U.S. PATENT DOCUMENTS

| | | |
|---|---|---|
| 6,138,476 A | 10/2000 | Watanabe et al. |
| 6,652,163 B2 | 11/2003 | Fajardo et al. |
| 2005/0008291 A1 | 1/2005 | Baney |
| 2005/0207455 A1 | 9/2005 | Maccormack et al. |
| 2008/0094636 A1 | 4/2008 | Jin et al. |
| 2011/0097045 A1 | 4/2011 | Benabid |
| 2014/0105554 A1 | 4/2014 | Schermer et al. |
| 2016/0258876 A1* | 9/2016 | Al Hosani ................ G01J 3/42 |
| 2017/0123147 A1* | 5/2017 | Brown ................ G02B 6/3652 |

OTHER PUBLICATIONS

IEEE—Photonics Letters, 2005, Yablon et al.

* cited by examiner

*Primary Examiner* — Tri T Ton
(74) *Attorney, Agent, or Firm* — Patricia Brzostowicz; Superior Patent Group LLC

(57) ABSTRACT

A robust and rugged method for sensing atoms and molecule using a small hybrid Hollow-Core Photonic Bandgap Fiber (HCPBF) is described. The hybrid fiber and associated chamber apparatus is amenable to mass production and can be used for wavelengths of light from 400 nm to 2000 nm.

8 Claims, 7 Drawing Sheets

METHOD FOR ATOMIC AND MOLECULAR SENSING

REFERENCE TO RELATED APPLICATIONS

The present application is a utility application under 35 USC § 101. It claims priority to U.S. Provisional Application Ser. No. 62/250,456 filed Nov. 3, 2015 and is a continuing application of U.S. application Ser. No. 15/341,646 filed Nov. 2, 2016 of common inventorship.

FIELD OF INVENTION

The present invention is drawn to the field of fiber reference chambers, in particular, the use of Hollow-Core Photonic Bandgap Fiber (HCPBF) and method of making a robust HCPBF reference chamber.

BACKGROUND

The use of glass reference cells filled with either a molecular gas or atomic vapor is a relatively old technology. Glass chambers or cells filled with gases or atom vapors are used by both commercial and military systems. Alkali metal filled glass cells such as those with rubidium, cesium, potassium, and sodium are used to frequency stabilize diode lasers. Molecular glass cells including acetylene, carbon monoxide, hydrogen cyanide, and methane cells, are the frequency reference standard for the telecom and gas sensing industry. These glass cells work well in a controlled environment but are not durable or stable enough for field use. Further, they are limited to absorption path lengths of 200 mm. In addition, they are fragile and bulky. There is a need for rugged and compact reference chambers with longer path lengths.

BRIEF DESCRIPTION OF THE INVENTION

The applicant's proposed solution is a robust fiber chamber for atomic and molecular sensing. Presented herein is such a fiber chamber and method of making thereof. The robust long path length frequency reference fiber cell of the present invention can be made using a Hollow-Core Photonic Bandgap Fiber (HCPBF) (NKT Photonics A/S Birkerod, Denmark). It can replace conventional glass reference cells and surpass their usefulness due to the small size. Further, the method of production of these cells is amenable to mass production processes.

Figure 1:
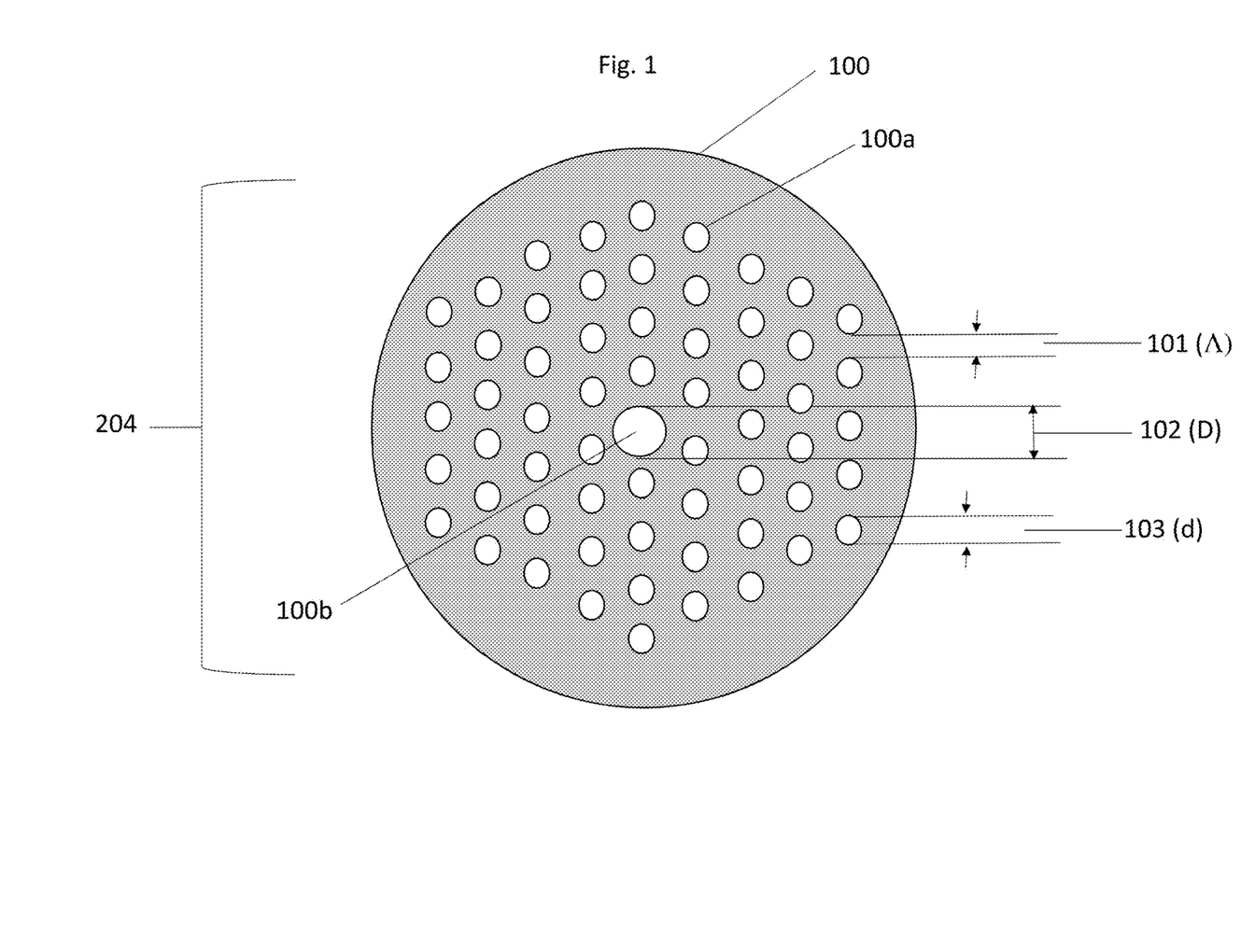
FIG. 1 is a schematic drawing of the interior of a Hollow-Core Photonic Bandgap Fiber (HCPBF).

Conventional fibers guide light by total internal reflection with the cladding layer index less than the core layer index. For a conventional fiber to accept gas the interior core must be air and a cladding material with an index of less than one, the index of air. A material with an index of less than one does not exist. Hollow waveguides fibers fabricated for infrared transmission can be filled with gas but they are multimode and not suited for coupling to single mode fibers. The inventors recognized that HCPBFs, having holes in the core as illustrated in FIG. 1, may be an ideal vessel to contain a gas which may be used as a frequency reference. These HCPBFs 100 confine light at specific frequencies by coherently backscattering light into the inner core 100b. The inner core 100b is hollow and can be filled with either atoms, alkali metals, or molecular gases but unlike infrared hollow waveguides they are also single mode and can be fusion spliced to standard single mode fibers.

In summary, the invention claimed is an apparatus comprising at least one HCPBF segment, wherein the HCPBF segment is cleaved to form two HCPBF pieces, at least two solid core fiber segments fused to the distal ends of the HCPBF pieces, and a mount, wherein the fused pieces are connected to the mount in a permanent way. In an alternate embodiment, the apparatus may comprise two HCPBF segments fused to two solid core fiber segments at distal ends. A GRINS lens or micro lens may be used to fuse the HCPBF segments or pieces to the solid core fiber segments. The apparatus may further comprise a hermetically sealed chamber wherein the mounted fibers are secured therein. Distal ends of the hollow core fibers from each of the more than one hermetically sealed chambers may be fused. In another embodiment, at least two hermetically sealed chambers containing the fused, mounted fiber segments, may be fused to form a multi-chamber apparatus. Alternately, the at least two sealed chambers may be connected with a continuous HCPBF segment to allow flow from one chamber to the other. Further, the chambers may comprise a light absorbing material being an atom or molecule. The mount may be in the form of a V mount or U mount. The solid core fiber may comprise a single- or multi-mode fiber.

Another embodiment of the present invention is a method for constructing a HCPBF chamber, the method comprising the steps of splicing a segment of HCPBF to a solid core fiber at each distal end, creating a gap in the segment of HCPBF, mounting the gapped HCPBF segment in a permanent manner, and securing the mounted gapped HCPBF segment in a chamber in a permanent fashion, wherein the chamber is hermetically sealable and includes a sealable port. This method may further comprise the step of evacuating the sealed chamber and filling the sealed chamber with a light absorbing material. The light absorbing material may comprise an atom or molecule and a light source may be coupled to the solid core fiber.

DETAILED DESCRIPTION OF THE INVENTION

Although there have been several research papers describing processes for using HCPBF as a reference cell, no rugged, compact, easily manufactured commercial product exists. Techniques attempted have not produced a small HCPBF cell that is robust, rugged, and amenable to mass production. The technology to produce HCPBF cells in bulk quantities has not existed. The applicants have invented a new HCPBF apparatus and method of making the same for applications requiring reference cells that are robust, rugged, small, and may be mass produced. For purposes of the present invention a reference cell or chamber is a hermetically sealed enclosure containing atoms, molecules, or evacuated space wherein a light source may pass therethrough for absorption of the light by the atoms or molecules.

Figure 2A:
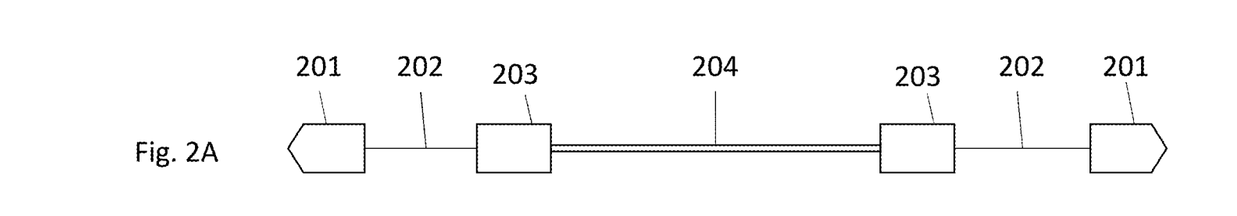
FIGS. 2A-2C are schematic drawings illustrating the apparatus and method for making a robust fiber cell.
Figure 2B:
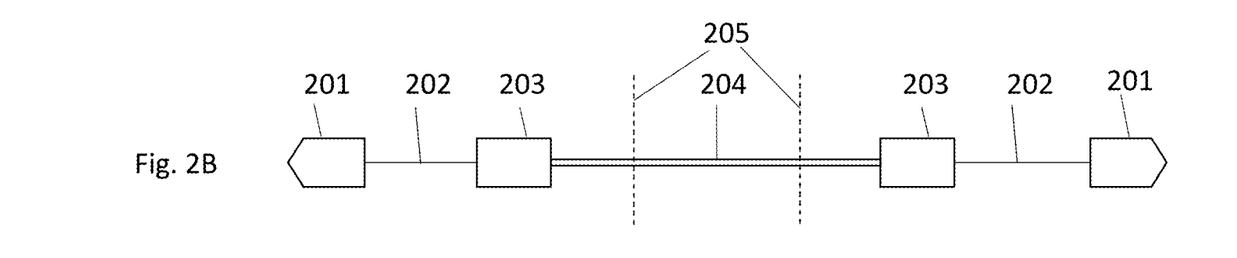
Figure 2C:
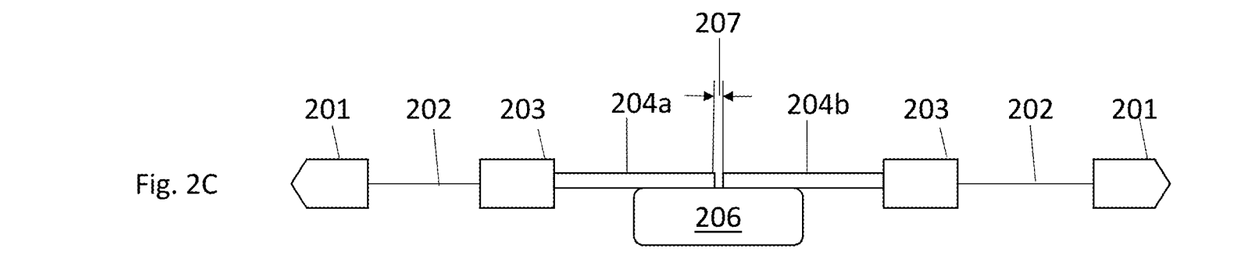

The present invention comprises the apparatus essentially as depicted in the drawing of FIG. 2C including at least one HCPBF segment 204 cleaved to form two pieces 204a, 204b. The distal ends of the HCPBF pieces 204a, 204b are fused to two solid core fiber segments 202 and a mounting device 206 permanently hold the segments in the desired configuration. In an alternate embodiment, the apparatus may be formed from two independent HCPBF segments. The solid core fiber 202 may be a single- or multi-mode fiber.

Figure 2D:
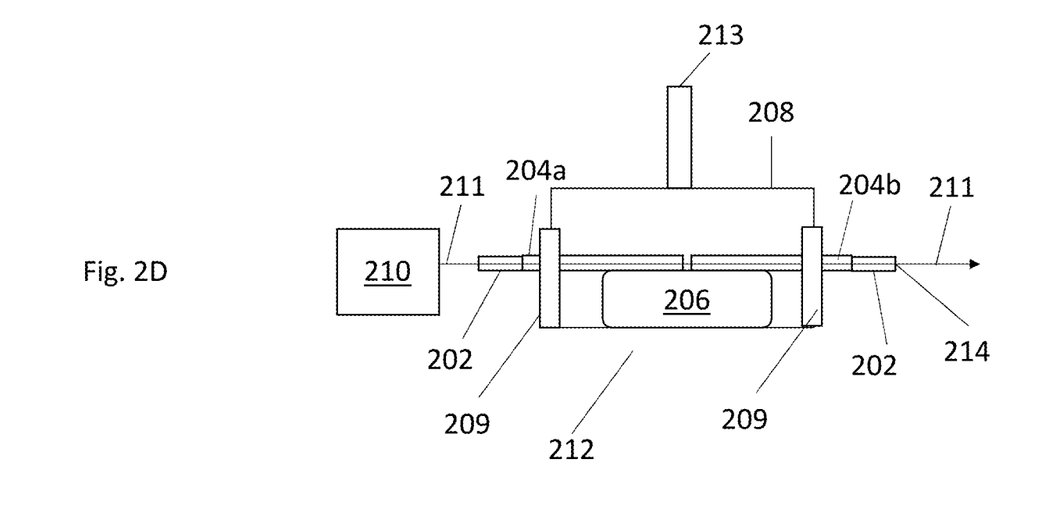
FIG. 2D is a schematic drawing of a robust fiber chamber.

The apparatus of FIG. 2C may be secured in a chamber 208 capable of being hermetically sealed as shown in FIG. 2D. The chamber includes a sealable port 213. Optionally the chamber may contain a window 209. The material used to construct the chamber may be, but not limited to, glass, metal, or ceramic. The chamber may be as small as about 1 $mm^3$, or even 1 $cm^3$, or even 1 $inch^3$, or larger depending on the application. In use, the solid core fiber 202 of the apparatus depicted in FIG. 2D may be coupled to a light emitting device 210 such that a light source 211 may be transmitted through the solid core fiber 202 into/through the HCPBF pieces 204a, 204b.

Figure 3:
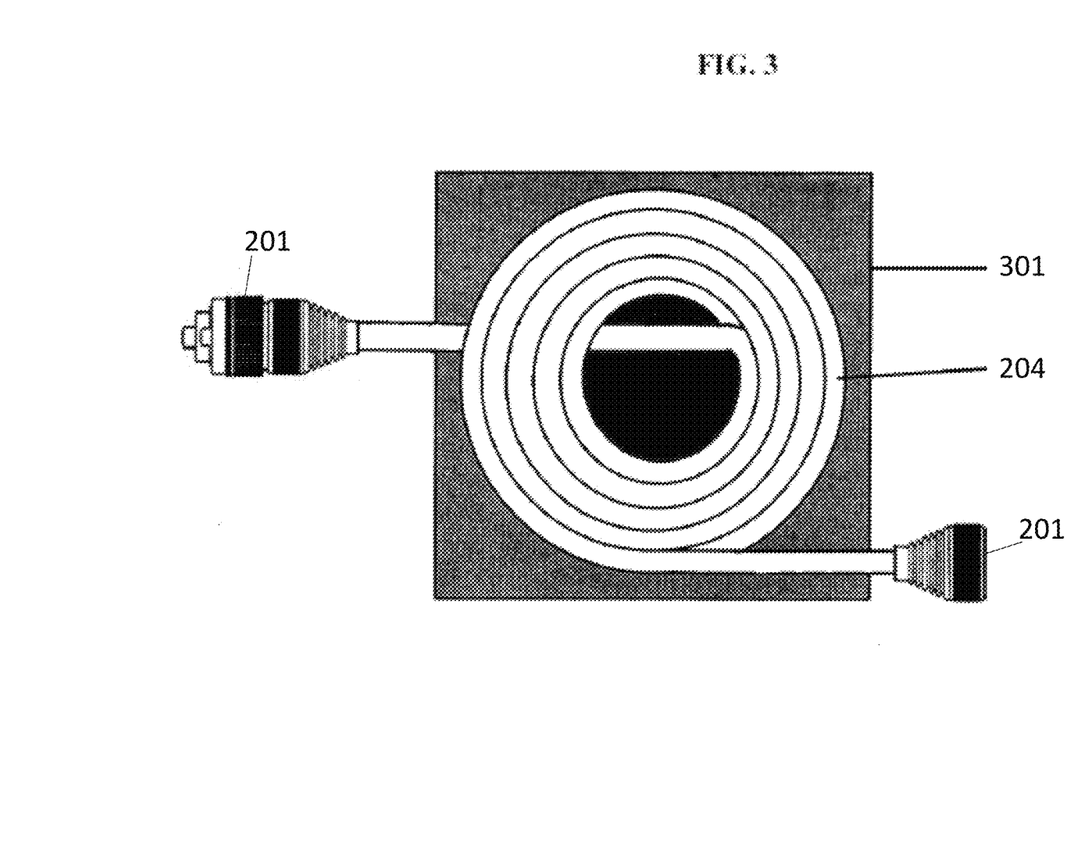
FIG. 3 is a schematic drawing of the apparatus as an in-use prototype.

As seen in FIG. 1, a representation of the cross section of a HCPBF 204 or 100, the HCPBF contains hollow spaces represented here as white spheres 100a. As is illustrated in the drawing, a HCPBF 204 is created by stacking hollow fibers in a hexagonal pattern spaced to scatter light back coherently into the hollow core 100b at certain wavelengths. By controlling the pitch, or distance between each hole in the fiber (A) 101, the diameter of the fibers, d, 103, and the core diameter, D 102, a HCPBF can be designed to transmit any wavelength between 400 nm and 2000 nm. Because the HCPBFs have low bending losses, a long fiber can be coiled into a very small space as can be seen in FIG. 3, described below. The inventors have exploited this advantage to create compact low pressure gas chambers with very long path lengths from HCPBFs as is illustrated in the description and included drawings.

FIGS. 2A-2E represent a method for creating the devices of FIGS. 2C-2D, and FIGS. 4-5. FIG. 2A is a schematic drawing illustrating splicing or fusion 203 of an HCPBF segment 204 to solid core fiber segment 202. Fusion or splicing herein refers to bonding of pieces to each other in a secure manner. To form the fiber that will transmit light, a segment of HCPBF 204 is spliced at the distal ends with two segments of solid core fiber 202. Examples of solid core fiber may include the single-mode fiber SM28, or a multi-mode fiber. These solid core fibers 202 may have connectors or couplers 201 at each end for light transmission. Alternately, the connectors may be added later. Fusion splicing the HCPBF 204 to the solid core fiber 202 may be achieved by use of a Gradient index lens, or GRIN lens, or similar coupling optics 203 including but not limited to a micro lens. The use of the GRIN lens 203 to fuse the HCPBF to the solid fiber may lower the transmission losses from the transition from HCPB fiber to solid core fiber.

Figure 2E:
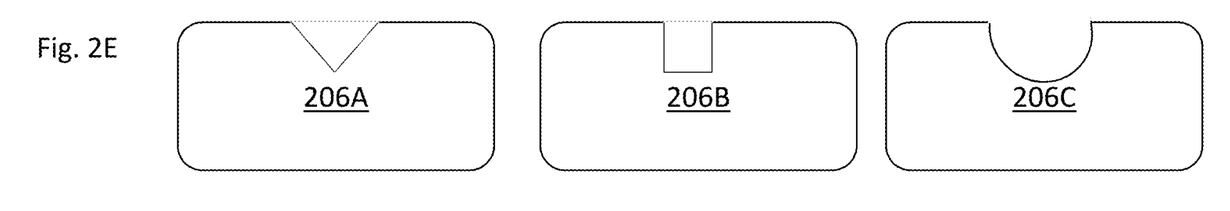
FIG. 2E is a schematic drawing of three different mount types.

As illustrated in FIG. 2B, the HCPBF 204 can be cut 205 to produce two HCPBF pieces 204a, 204b with open ends. The HCPBF segment may be cut using a fiber cleaver or any tool intended as a fiber cutter. Alternately, two segments of a HCPBF fiber could be used wherein no cut would be needed. In FIG. 2C, the open proximal ends of the HCPBF pieces 204a, 204b may be brought into close proximity to one another and aligned using a mounting block 206. The mounting block 206, as illustrated in FIG. 2E, may be a V block design 206A, or a U block design 206B or 206C, such that the HCPBF pieces 204a, 204b rest with ends properly oriented such that the holes in the fiber are aligned as they were before splicing in the bottom of the V. A V mounting block 206A is a block of material having a precise V shaped groove. V blocks are often used for checking concentricity of circular parts and for holding cylindrical pieces in precise alignment.

In FIG. 2D, a light emitting device 210 may emit a light source 211 into the solid core fiber 202 and through the HCPBF pieces 204a, 204b. Light sources may include but are not limited LED, laser, or free space light, coupled through an optical collimator 201 or similar focusing optical component, or a fiber coupled light source connected to the fiber connector 201 (illustrated in FIGS. 2A-2C). Prior to forming the HCPBF chamber, the HCPBF segment may be tested for transmission by measuring light emitted through the opposite end of the fiber. Once good transmission is verified, a mid-section of the HCPBF 204 is cleaved off 205, as depicted in FIG. 2B, or the HCPBF segment 204 is cleaved in half, so that the fiber ends are at ninety degrees to the surface of the mounting block 206. In this manner pieces 204a and 204b are formed. Any lateral misalignment in the block will causes a loss in transmission of light through the HCPBF pieces 204a, 204b. Cleaving the fiber to create two ends, versus using two separate fibers, minimizes any lateral misalignment since both HCPBF 204a, 204b pieces are the same diameter and have the same internal structure. The ends need to be inspected with a microscope, preferably a high-powered microscope, to make sure the hole structure (see FIG. 1) at the proximal ends of the fiber pieces 204a 204b is not damaged. If the fiber ends are not damaged, the HCPBF-solid fiber fused pieces are mounted to the V block 206 and bonded in close proximity so that there is a gap 207 between the fiber ends, as shown in FIG. 2C. The gap 207 may be about 1 μm in distance or larger. The larger the gap the more light that will be lost. Low temperature glass or adhesive may be used to permanently bond the apparatus to the mounting block 206.

As illustrated in FIG. 2D, the apparatus of FIG. 2C may be enclosed or partially enclosed in a chamber 208. The HCPBF pieces 204a, 204b will extend through the walls of the chamber 208 which may include a pane 209. A fusion splicer may be used to fuse the HCPBF pieces 204a, 204b with the hermetically sealed chamber. The interior space 212 of the chamber 208 may be vacuumed and re-filled with any number of gaseous particles, atoms, molecules, ions, or the like through a sealable fill stem 213. In alternate embodiments, the space 212 may be left with a vacuum. A sealable port 213, fused to the chamber 208, is used to pass a vacuum or gases through to the interior of the chamber 212.

Since the fiber ends are formed from the same fiber 204 they are concentric with each other. With the ends secured in the mounting block 206, a light source 211, emitted from a light emitting devices 210, will travel thru one side of the fiber across the air gap with most of the light coupling into the opposing fiber and through the end of the fiber 214. In fact, in this apparatus, pictured in FIG. 2D, the light will jump the gap with only a small loss in transmission. The HCPBF fiber-grin lens-solid core fiber apparatus will act as a continuous fiber. Any loss of transmission of light jumping the air gap may be calculated by measuring the transmission from fiber connector to fiber connector. The transmission difference between transmission of light through a continuous un-cut HCPBF and the apparatus formed in FIG. 2D, is the light lost from light passing thru the air gaps. The transmission loss due to the air gap is approximately:

$$\text{Loss} = 1 - e^{-\left(\frac{n_0 \pi \omega_0}{\lambda} \sin(\theta)\right)^2}$$

$n_0 = 1$ index outside of fiber

Given a cleave tolerance of +/−0.5 degrees and a separation of the two ends of the same fiber of 10 microns, the calculated approximate splice loss of no more than about 10 percent, or even no more than about 5 percent, or even no more than about 2 percent, or even no more than about 1 percent.

As shown in FIG. 2D, the mounting block-fiber apparatus may be mounted on the bottom of a chamber 208 or otherwise secured. The mounting block 206 which holds the fibers 204a, 204b are secured to interior chamber wall in a permanent fashion. The fiber enters the chamber thru one wall and exits through another. The side walls are then sealed at the junctions with the HCPBF going through them. Once the chamber is completely sealed, for example hermetically sealed, the cell's fill stem may be paired 213 with a pump. The chamber is pumped out and then may or may not be back filled with a fill material. The fill material may be a molecular gas, with non-limiting examples being methane, ethane, and carbon dioxide, or an alkali metal vapor such as rubidium or cesium, or the like, gaseous atom, or other atoms or molecules.

A finished HCPBF gapped apparatus formed by the above method may be as short as about 0.5 cm in length or as much as about one meter in length or more, but can easily be coiled to fit on a one inch square circuit board as illustrated in FIG. 3. Therefore, the size of the chamber 208 (FIG. 2D) may be anywhere from about 1 mm³, to 1 cm³, or about 1 inch³, or about 2 inch³, or more.

In FIG. 3, a square circuit board 301 is fitted with the HCPBF gapped apparatus in a coil pattern. The ends of the solid core fibers are fitted with fiber connectors 201. The gap in the HCPBF is not shown but would be achieved in a manner similar to that described above. An alternate embodiment of the invention is to fill the HCPBF with gas or fill material prior to the step of fusing the GRIN lens and solid core fiber pieces to the ends.

Figure 4:
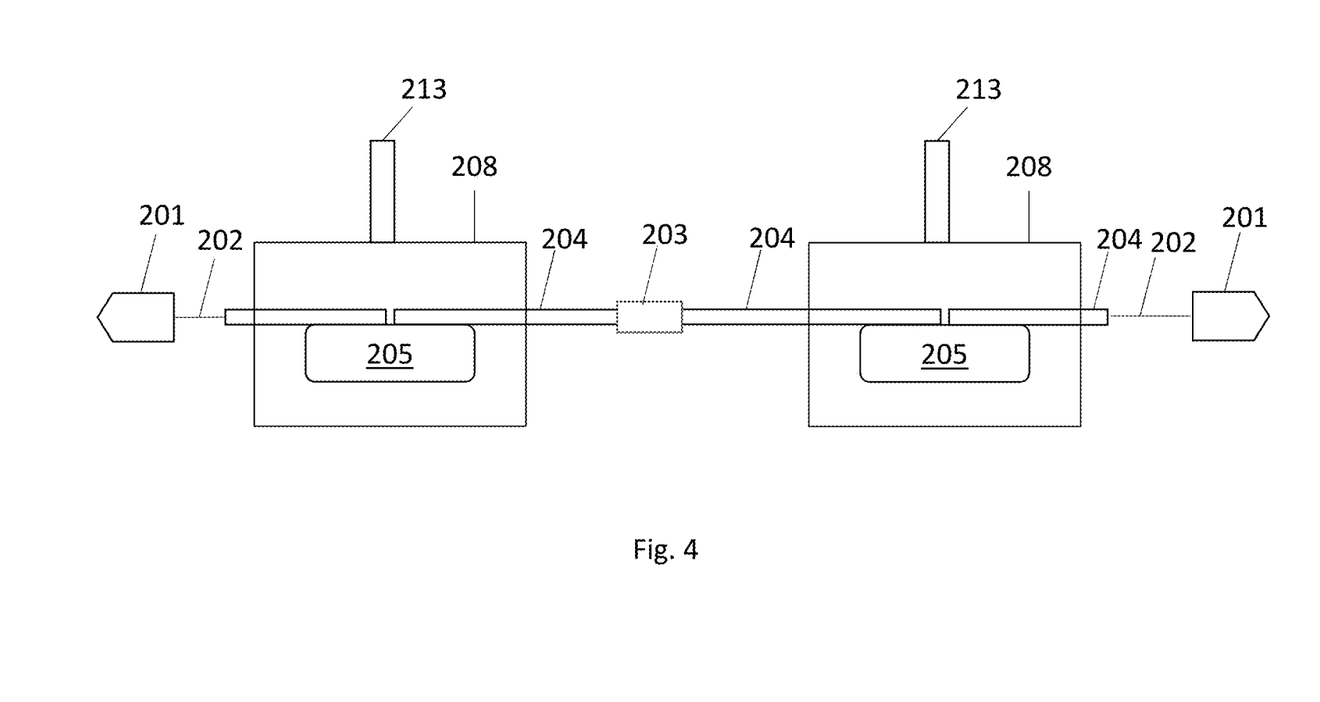
FIG. 4 is a schematic drawing of an alternate embodiment of the apparatus.

As shown in FIG. 4, two or more HCPBF chambers may be arranged in series. A HCPBF 204 of one chamber may be fused with the HCPBF of another chamber 204 using a GRIN lens or other fusion mechanism 203. This allows a single light emitting device and light source (not shown) to pass through a coupling means 201 and the solid core fiber 202 into the HCPBF 204 and through both chambers 208. The chambers 208 may be contain the same or different fill material to either assess different variables or have duplicate test. Alternately, one chamber may be filled with material to be used as a fixed reference cell. In this embodiment, the separate HCPFB segments of each chamber 204 are fused or spliced together 203 to form one apparatus but no fill material would pass between the two chambers.

Figure 5:
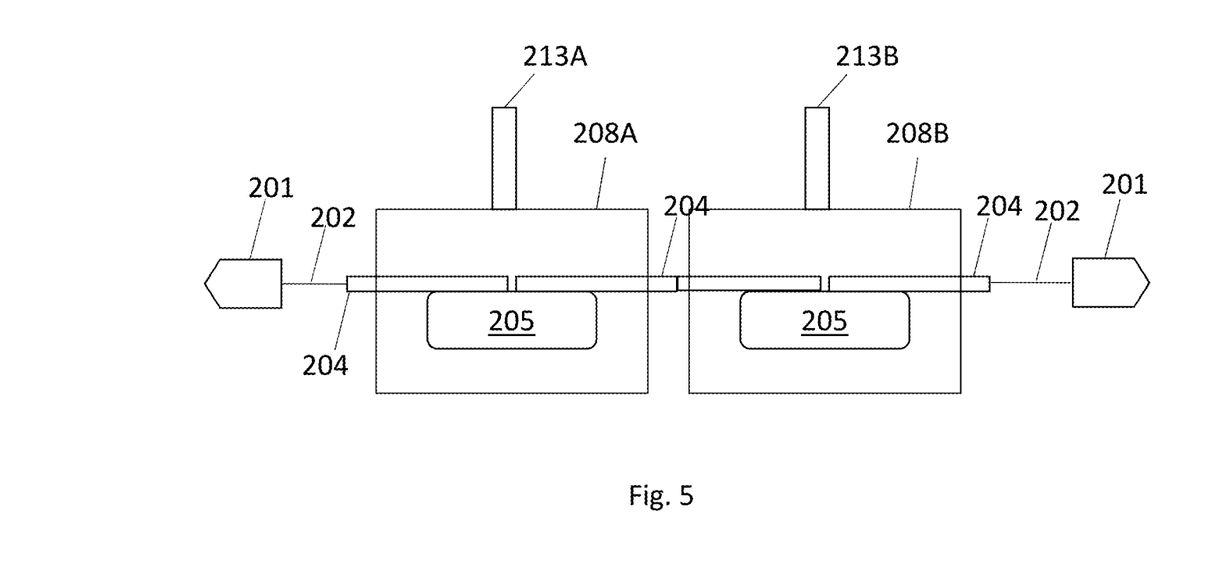
FIG. 5 is a schematic drawing of another embodiment of the apparatus.

An alternate embodiment is shown in FIG. 5 wherein a continuous segment of HCPFB 204 allows fill material to flow from one chamber to another. The fill stem(s) 213A, 213B may be left open for use as a flow cell to measure a contaminant. In another example, one fill stem 213A may be fitted with a pump to introduce a fill material into 208A and a second fill stem 213B may be fitted with a vacuum to pull fill material through 208B and out 213B. As in FIG. 4 this allows use of a single light emitting device and light source (not shown).

EXAMPLE

Figure 6:
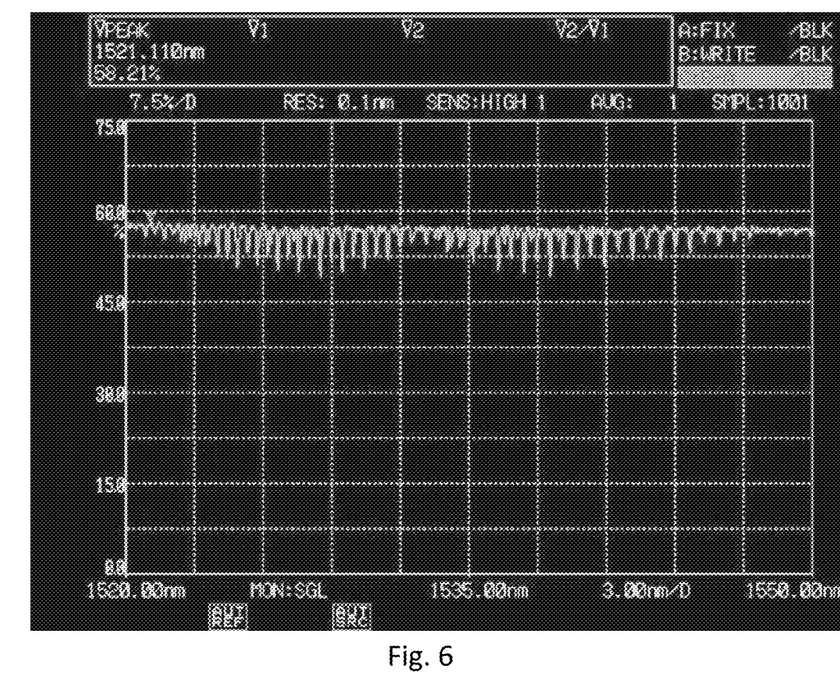
FIG. 6 is an example absorption scan.

As an example of our process we hermetically encased an apparatus as described and shown in FIG. 2C inside a chamber. The chamber was a 4 mm by 4 mm glass microcell with a fill stem in the middle. The microcell was initially assembled without the bottom window. The bottom window was attached once the mount, being a V mount microgroove, was fitted with the HCPBF-solid core fiber assembly of FIG. 2C and secured to the window. In this experiment, we chose a NKT Hc-1550-02 HCPBF (NKT Photonics, Birkerod, Denmark) and a fill material of acetylene isotope 13 gas. The HCPBF was cleaved into two pieces approximately 50 mm in length. The distal ends of the HCPBF were then fused to a 1550 nm single core fiber. In this example the light source was a SL diode with FC/APC connection output. The model number BWC-SLD light source is manufactured by B&W Tek (Newark, Del., USA). Each of the single mode fiber ends were terminated with compatible FC/APC connectors. The HCPBF was fitted in the cell in the side windows through glass capillary tubes. The HCPBF piece ends were aligned with a spacing of approximately 15 microns and permanently attached to a V mount microgroove. The V mount assembly was attached to the microcell bottom window. The bottom window of the microcell was placed on the microcell body. Any excess HCPBF was pulled thru the capillary tubing. With the bottom window attached to the microcell body, the HCPBF was sealed inside the microcell by heating the glass capillary tubes and shrinking them around the outer cladding of the fiber. The fill stem was hooked up to a vacuum pump and the microcell was evacuated and back filled with acetylene 13 gas. The SL diode light emitter was connected so that the light source passes thru one end of HCPBF. The other HCPBF end was attached to Ando AQ-6315A Optical Spectrum Analyzer (Ando Corporation, Tokyo, Japan). The analyzer was used to measure the absorption of the acetylene 13 gas. FIG. 6 shows the absorption scan of acetylene 13 gas. In the graph, the X axis depicts the wavelength of light. The y axis shows the transmission percentage wherein the baseline represents the output when one hundred percent of the light is collected. The transmission level dips as the acetylene gas absorbs the light at the given wavelength.

While various embodiments and examples have been described in detail, it is apparent that modifications and adaptations of those embodiments will occur to those skilled in the art. However, is to be expressly understood that such modifications and adaptations are within the spirit and scope of the present disclosure.

We claim:

1. A method for constructing a HCPBF chamber, the method comprising of the steps of:
   a) splicing a segment of HCPBF to a solid core fiber at each distal end;
   b) creating a gap in the segment of HCPBF;
   c) mounting the gapped HCPBF segment in a permanent manner;
   d) securing the mounted gapped HCPBF segment in a chamber in a permanent fashion;
   e) hermetically sealing the chamber; and
   f) fixing a sealable port in the chamber wall, wherein no light is generated by construction of the HCPBF chamber.

2. The method of claim 1, further comprising the step of evacuating the sealed chamber.

3. The method of claim 2, further comprising the step of filling the sealed chamber with a light absorbing material.

4. The method of claim 3 wherein the light absorbing material is an atom.

5. The method of claim 4 wherein the light absorbing material is a molecule.

6. The method of claim 5, further comprising the step of coupling a light source to the solid core fiber.

7. The method of claim 6, further comprising applying a light source to one end of the HCPBF.

8. A method for sensing atoms or molecules, the method comprising the steps of:
   a) splicing a segment of HCPBF to a solid core fiber at each distal end;
   b) creating a gap in the segment of HCPBF;
   c) mounting the gapped HCPBF segment in a permanent manner;
   d) securing the mounted gapped HCPBF segment in a chamber in a permanent fashion;
   e) hermetically sealing the chamber;
   f) fixing a sealable port in the chamber wall, wherein no light is generated by construction of the HCPBF chamber;
   g) evacuating the chamber;
   h) filling the chamber with a gaseous light absorbing material;
   i) coupling a light source to one end of the HCPBF;
   j) filling the chamber with a test sample; and
   k) measuring an amount of light absorption.

\* \* \* \* \*